United States Patent [19]

Dufresne et al.

[11] Patent Number: 5,745,227
[45] Date of Patent: Apr. 28, 1998

[54] METHOD AND APPARATUS FOR DETERMINING THE ERYTHROCYTE SEDIMENTATION RATE

[75] Inventors: Christopher Dufresne, Maastricht, Netherlands; Georges Bonnevial, Le Cheylas; Jean Emin, Saint Etienne de Crossey, both of France

[73] Assignee: Becton, Dickinson and Company, Franklin Lakes, N.J.

[21] Appl. No.: 670,475

[22] Filed: Jun. 26, 1996

[30] Foreign Application Priority Data

Jul. 21, 1995 [EP] European Pat. Off. ............ 95111491

[51] Int. Cl.[6] .......................... G01N 15/05; G01N 33/49
[52] U.S. Cl. ............................................ 356/39; 436/70
[58] Field of Search .................... 356/246, 39, 240; 436/70

[56] References Cited

U.S. PATENT DOCUMENTS

| | | | |
|---|---|---|---|
| 4,045,175 | 8/1977 | Weber | 436/70 |
| 4,474,056 | 10/1984 | O'Brien et al. | 73/61.4 |
| 4,848,900 | 7/1989 | Kuo et al. | 356/39 |
| 5,003,488 | 3/1991 | Hardy | 364/509 |
| 5,594,164 | 1/1997 | Bull | 356/246 |

FOREIGN PATENT DOCUMENTS

| | | | |
|---|---|---|---|
| 0 044 822 | 1/1982 | European Pat. Off. | B01L 3/14 |
| 0 265 596 | 5/1988 | European Pat. Off. | G01N 15/05 |
| 0 454 593 | 10/1991 | European Pat. Off. | G01N 33/48 |
| 2 394 797 | 6/1978 | France | G01N 21/48 |
| 2 566 126 | 6/1984 | France | G01N 15/05 |
| 2 652 416 | 9/1990 | France | G01N 15/05 |
| 2 153 072 | 8/1985 | United Kingdom | G01N 15/05 |
| 35 29 455 | 3/1986 | United Kingdom | G01N 1/10 |

*Primary Examiner*—Richard A. Rosenberger

[57] ABSTRACT

In an improved method for measuring the erythrocyte sedimentation rate (ESR) a pre-evacuated test tube (T) is used to collect a blood specimen. The tube (T) is made of a material such as glass or plastics and contains an anticoagulant/mixing agent. For testing, the tube (T) is put into a rack (1) and loaded into an instrument which mixes the specimen briefly. An optical sensor (3) is used to record the location of the blood/air meniscus at initial time. At subsequent time intervals thereafter for periods up to 20 minutes or less, the optical sensor (3) identifies and measures the location of the cell/plasma interface (I) within an observation window constituting a minor portion of the overall length of the tube (T). The measured value is then converted by an algorithm (10, 11) to the value which would be obtained using the classical Westergren method.

7 Claims, 7 Drawing Sheets

METHOD AND APPARATUS FOR DETERMINING THE ERYTHROCYTE SEDIMENTATION RATE

The present invention relates generally to determining the erythrocyte sedimentation rate (ESR) in a blood sample. The standard laboratory method heretofore used for measuring ESR is the so-called Westergren method. A general review of that method is provided in "ICSH recommendations for measurement of erythrocyte sedimentation rate" published in Journal of Clinical Pathology 1993; 46: 198–203.

Essentially, the Westergren method provides for a sample of blood to be collected in a test tube (pipette) to form a 200 mm blood column in the presence of an anticoagulant. After mixing the specimen briefly, the test tube is loaded into a device or an instrument including sensors such as an optical sensor to record the location of the blood/air meniscus at an initial time. After a period of 60 or 120 minutes, the operator or the sensor then identifies and measures the location of the cell/plasma interface. The distance in millimeters from initial blood/air meniscus and the final cell/plasma interface gives the typical Westergren output value for the test which is expressed in units of mm/hr.

A basic disadvantage of the conventional Westergren method lies in the considerable length of the test tube (typically in excess of 200 mm) which makes it unsuitable for use in collecting blood directly. Consequently, blood for the test has to be taken either by using a syringe or a pre-evacuated tube and the blood thus collected must then be transferred to the Westergren test tube. In addition to being unpractical, such a procedure exposes the operator to the danger of contacting the blood during the transfer process.

Systems dispensing with such a drawback and carrying out ESR determination using tubes significantly shorter than the standard 200 mm Westergren pipette are already available.

Exemplary of such prior art is, for instance, the ESR measuring system sold under the trademark SEDISCAN by the assignee of the present application. A SEDISCAN instrument is adapted for use in connection with tubes (sold under the trademark SEDITAINER—both SEDISCAN and SEDI-TAINER being registered trademarks of Becton Dickinson and Company) essentially comprised of 5 ml draw tube of 120 mm length and 10.25 mm outer diameter containing liquid sodium citrate/citric acid at 4:1 ratio. Using the above tube, the SEDISCAN instrument provides an extrapolated Westergren value after 30 minutes which compares well to actual 60 and 120 minutes Westergren values. However, it is necessary to examine nearly the entire tube length (about 70–80 mm of the blood column height of 100 mm) in order to predict the ESR. The tube is held vertically.

Another system using "short" tubes is sold under the trade name VESMATIC by the Italian company Diesse Diagnostica Senese S.r.l.. The tube for use in this latter system has a rectangular shape overall and a triangular shape of the tube bottom. Again, nearly the entire tube length must be scanned which leads to using an additional plastics outer sleeve to apply patient bar code or identification labels. The outer sleeve and the patient identification data must be removed from the tube before this is placed in the instrument for carrying out the test. Consequently, there is an actual danger that, due to the high number of tubes tested concurrently in a laboratory, a diagnostic result may be incorrectly assigned to the wrong patient due to a mistake in association of the clinical result for a tube with the patient identification contained on the removed outer sleeve.

So, it is practically a mandatory requirement for any test tube for proper use in ESR measuring test to carry patient identification data which must not and cannot be removed at any time, while carrying out the test.

Also, there is a growing trend in the field of ESR determination to provide reading of the test final values in a significantly shorter time than the standard 60 minutes of the Westergren method. Finally, the quantity of blood required for the test (and consequently the quantity of blood to be taken from the patient) is to be made as small as possible.

The basic underlying problem of the present invention is providing a solution which jointly overcomes the drawbacks of the prior art solutions, i.e. by providing an ESR determination procedure, where:

"short" tubes are used, preferably adapted for direct blood collection;

patient identification data, once applied onto the tube, cannot be removed from it, thereby making it impossible to dis-associate the specimen from the patient identification;

reliable ESR values are provided in a term much shorter then the standard 60 or 120 minutes of the Westergren; and the quantity of blood to be taken from the patient is minimised.

In the presently preferred embodiment of the invention, a pre-evacuated test tube is used to collect the specimen which is made of such a material as glass or plastics and which contains an anticoagulant. The tube is then put into a rack and loaded into an instrument which mixes the specimen briefly. The instrument then uses optical sensors to record the location of the blood/air meniscus at an initial time. At subsequent time intervals thereafter for periods up to 30 minutes, typically 20 minutes or less, the optical sensors then identify and measure the location of the cell/plasma interface. These measured values are then converted by a given relationship, e.g. an algorithm, to the values which would be obtained using the classical Westergren method (200 mm blood column height and blood to citrate ratio of 4:1).

Further details concerning the tube T and the additives contained therein are provided in a parallel European Patent application filed on even date by the same Applicant of the present application.

The invention will now be described, purely by way of example, with reference to the annexed drawings, wherein.

Figure 1:
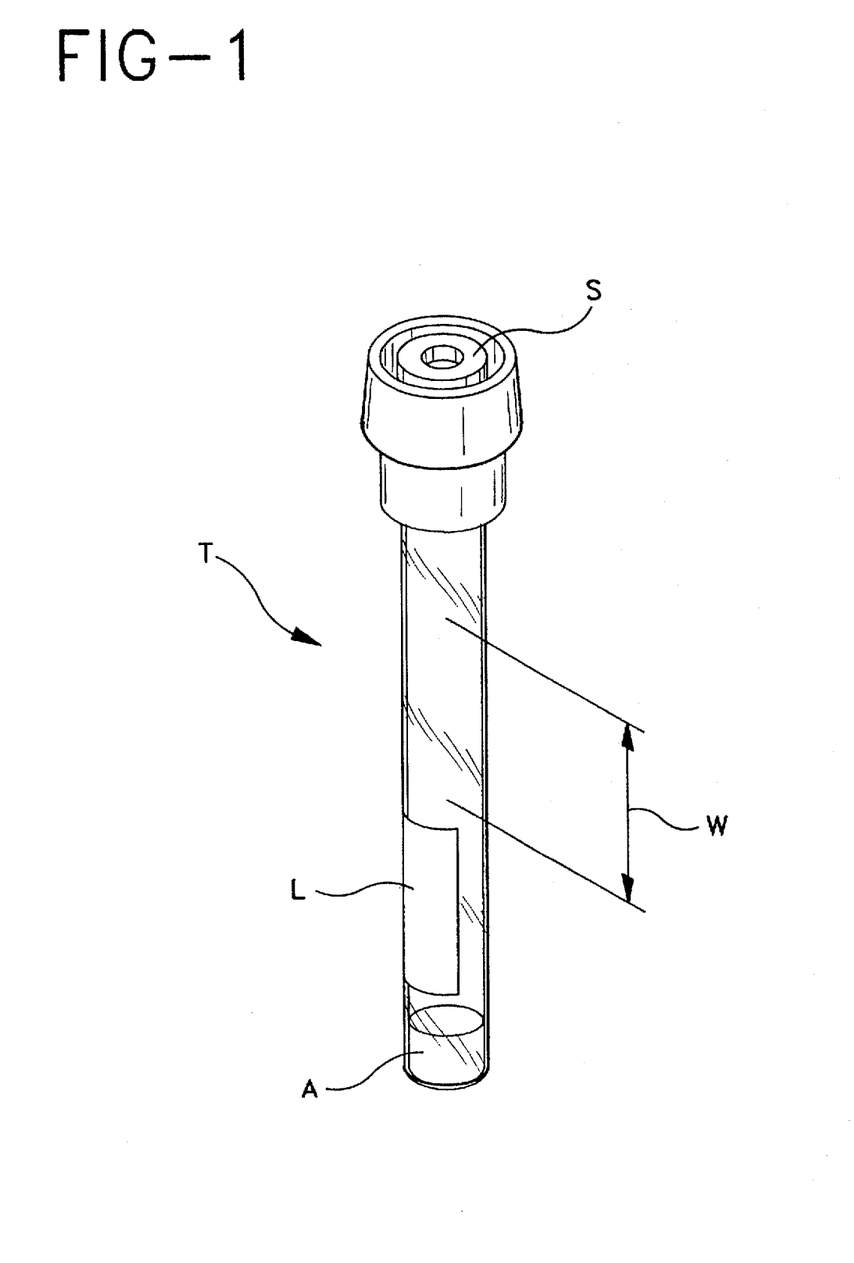
FIG. 1 shows a test tube according to the invention.

In FIG. 1 an exemplary tube according to the invention is generally designated T. The tube T, which may be typically constructed from glass or plastic, has a tubular, preferably cylindrical wall with an outside diameter of not less than about 7 mm and not more than about 9 mm. The length of the tube T (which roughly corresponds to the height of the blood column formed therein) is preferably not less than about 75 mm, but not more than about 105 mm and still preferably about 80 mm. The inside diameter is preferably not less than about 5 mm and not more than about 7 mm and still preferably about 6 mm.

However, it will be appreciated that the term "tube", as used herein and in the annexed claims, is not to be construed as strictly limited to the typical test tube (pipette) arrangement exemplified in FIG. 1. Even though the one shown is held at present to constitute the best mode of carrying out the invention, alternative arrangements can be devised, such as one where the tube is incorporated to an instrument or device adapted for collecting blood and then conveying it (e.g. by means of a pumping action) to a tubular member adapted for forming the blood column which is used for carrying out the test.

Irrespective of the specific embodiment, the inner diameter of the tube T must be sufficiently large to allow the blood specimen used for the test to mix adequately immediately after collecting to ensure complete anticoagulation is achieved. Subsequently, immediately before initiating the measurement of the ESR, the specimen must be uniformly and completely mixed to re-suspend blood cells.

An inner diameter below about 5 mm slows mixing to such a degree that clotting and cell aggregation occur subsequently, causing an unpredictable acceleration of the rate of cell falling during the ESR measurement and thus error in the correlation with the classical Westergren method.

The inner diameter and tube length should also be sufficiently small to minimise the volume of the blood required from the patient for the test, since excessive blood lost by patients is considered detrimental to their health. This is particularly the case for paediatric patients who have small blood volumes and geriatric patients who have diminished capacity to regenerate blood cells. In the configuration described, blood requirements would be typically less than 2 mils which is considered sufficiently small to have little impact on patient health.

The outer diameter and tube wall thickness must be sufficiently large to add sufficient strength and rigidity to ensure the tube does not break or bend during handling and subsequent testing. However, they should be sufficiently small to ensure the tube is easy to cut, form and glaze as in the case of a glass tube or injection moulded as in the case of a plastics tube. Excess material leads to higher manufacturing cost and an overly thick tube wall could reduce the ability of an optical viewing device to see through the wall when attempting to identifying the meniscus and the interface.

Optical imaging devices, such as a LCDs, linear CCDs and video cameras, are preferably used in connection with a visibly transparent tube wall (at least insofar as the "window" of the tube actually observed is concerned), e.g. made of glass or transparent plastics. Alternative embodiments can however be envisaged, wherein non-optical sensors and/or visibly opaque, non-transparent tube walls are used. Exemplary of such alternative embodiments are imaging devices operating outside the visible range (e.g. infrared radiation) or devices operating with other kinds of radiation or based on other physical phenomena (e.g. capacitive sensors and the like).

Optical devices are however preferred due to the current availability of devices adapted for use within the framework of the invention. Exemplary of such devices are, in addition to the one used in the assignee's SEDISCANR system, those sold under the trade names Sony CCB-M25/CE (CCD) and Sony PSB9151A (power board) [Sony, Kanafawa, Japan] and Computak 6 mm 1:1–2 ½" C (Lens from Japan).

The open end of the tube T is preferably sealed by a stopper S having vacuum and moisture barrier properties suitable to maintain the additive contents and blood drawing capability for periods in excess of two weeks and preferably for periods in excess of one year. The stopper S is preferably an elastomeric material such as bromobutyl or chlorobutyl rubber which is also easy to penetrate using a double-ended blood collection needle and which re-seals upon needle removal to prevent leakage of the specimen. The external diameter of the stopper S is preferably between about 12 and about 17 mm, such that it can be easily inserted into, centered on the needle and removed from a standard needle holder. Exemplary of such a stopper are the stoppers found on evacuated blood collection tubes and sold by the assignee company under the trademarks VACUTAINER®, BEMOGARD® and PLUS®.

The tube T according to the invention may be packaged and sold as a stand-alone, disposable, product comprised of the tube body proper (made of glass or plastics, for instance) pre-evacuated and sealed by the stopper S and also including a quantity of additive A. Primarily, the additive is intended to act as an anti-coagulating agent/mixing aid.

Preferably, the additive is a mixture of tri-sodium citrate ($Na_3$) and citric acid mixed in an aqueous solution to achieve a molarity of 0.105M–0.135M. Sufficient solution (e.g. 0.46 cc—referring to the preferred dimensions of the tube T referred to in the foregoing) is dispensed into the tube T during manufacturing in order to ensure a blood to additive ratio upon specimen collection of 4:1. However, when using liquid citrate solutions, blood to additive ratio starting at about 2:1 and below and up to about 10:1 and above are possible; the mathematical algorithm which converts the observed rate of cell settling to the classical Westergren value is adapted accordingly. Likewise, alternative anticoagulants such as EDTA, Hirudin and its analogues or potassium and sodium oxalate can be used in a variety of forms, such as liquid, freeze dried, powder or spray coatings. Each may be equally effective in anticoagulating the specimen without haemolysis and with an appropriate mathematical algorithm will allow conversion of the observed value to the Westergren value. Non-liquid, e.g. dry additives are usually preferred in the case of plastics tubes due to the well-known tendency of plastic tube to lose moisture.

Also, to further enhance and facilitate mixing of the specimen in the tube, a component which reduces the surface tension-of the blood is preferably added to the tube as a coating or combined with the anticoagulant in its liquid or dry form. Desirably, the surfactant is a nonionic surfactant. An example of such a surfactant is an organosilicone. Preferably, the organosilicone is a polyalkyleneoxide modified polydimethyl-siloxane. Polyalkyleneoxide modified polydimethyl siloxanes are found to be stable with irradiation, do not cause the blood to haemolysis and increases the rate of mixing the specimen to provide a well anticoagulated and homogeneous specimen without cell aggregation or clotting.

Generally, there is an exponential relationship between mixing time and concentration of surfactant, and at approximately 1% by weight the fastest mixing time was achieved.

Figure 2:
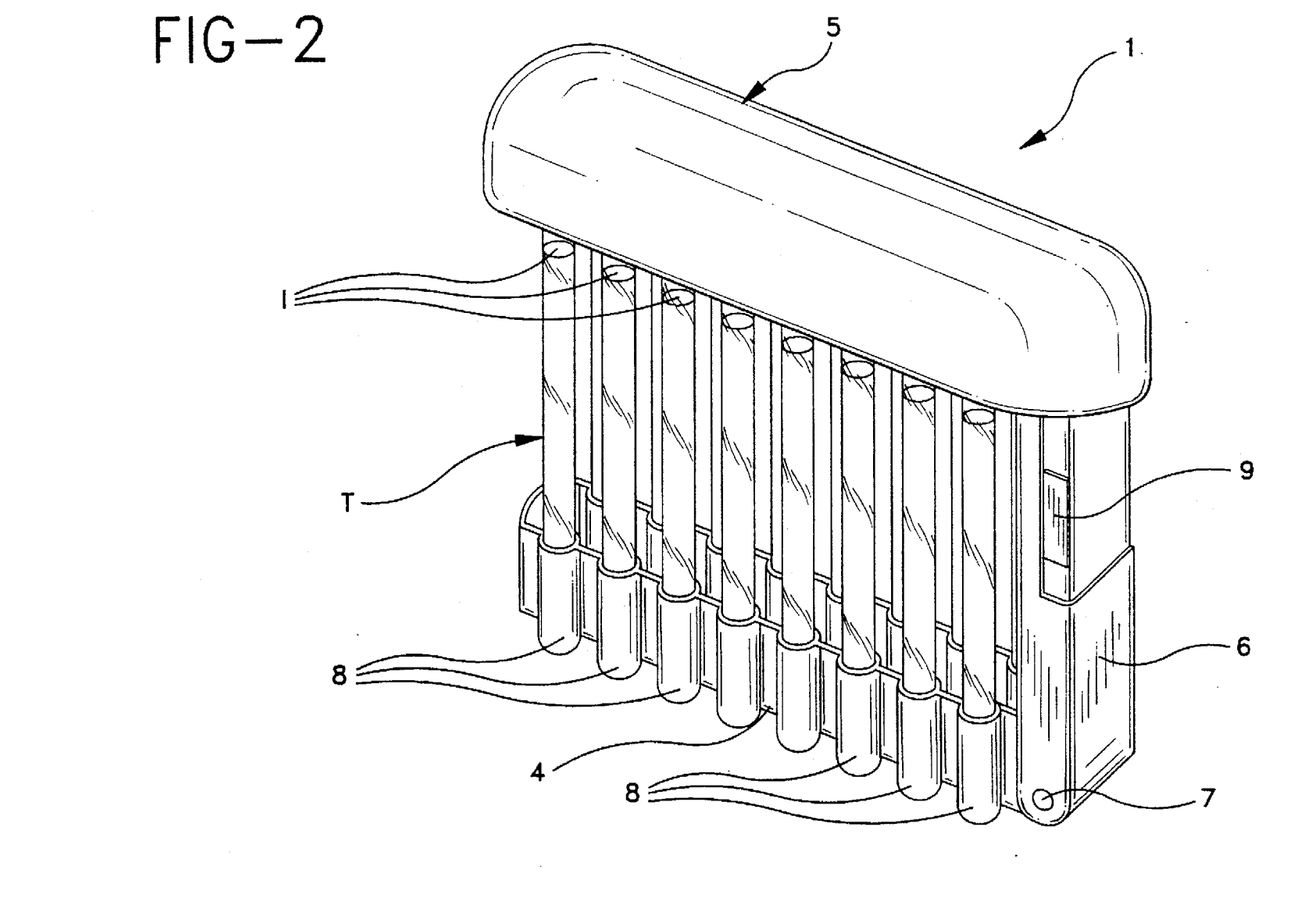
FIGS. 2 and 3 show diagrammatically the typical arrangement of device of the invention.
Figure 3:
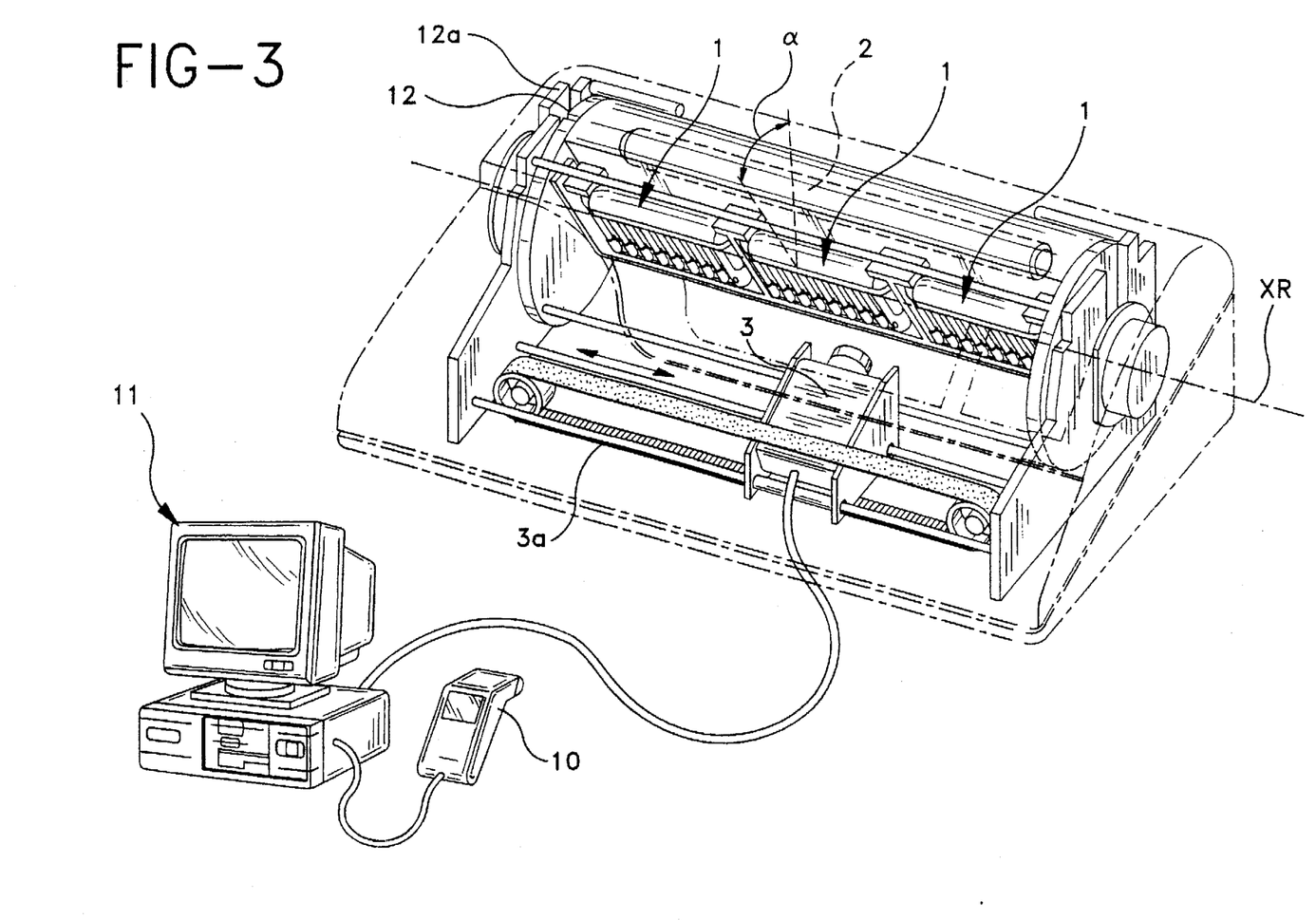

FIG. 2 and 3 show a rack 1 adapted for receiving one or, preferably, a plurality of tubes T, a light source 2, such as a fluorescence light arranged on one side of the rack 1 to create background illumination, as well as an optical imaging device such as a video camera 3, arranged on the other side of the rack 1 and adapted for viewing, as better described in the following, the tube or the tubes T against the background illumination created by the source 2.

The location of the cell/plasma interface (schematically designated I in FIG. 2) is thus detected as a contrasted image (dark/clear, black/white) against said background illumination.

In the preferred embodiment shown in FIG. 2, the rack 1 is essentially comprised of a C-shaped frame having opposite lower 4 and upper 5 arms adapted for securely receiving the lower and upper ends of the tube or tubes T. The two horizontal arms 4, 5 are connected by an upright arm 6 which is rigidly fixed to one of the arms (for instance upper arm 5) and is hinged at 7 to the other (in the present instance lower) arm 4. This arrangement permits the rack 1 to be opened to insert the or each tube T into respective cavities 8 provided in the lower arm 4 and then securely locked to their final position for carrying out the test by bringing the rack 1 to its closed position with the upper arm 5 (having respective cavities or a cutout on the lower side thereof—not visible in the drawing) to engage the upper ends of the tube or tubes T (closed by the stopper S). The rack 1 is then locked to its closed position by means of a lock mechanism controlled by a thumb-actuated slider 9.

According to an arrangement well-known per se, the camera 3 has associated therewith drive means (such as a motor-driven toothed belt 3a) which cause it to undergo a traverse movement (as shown by the double-pointed arrow of FIG. 3) along the tube or tubes T. The motor moves the camera to view each rack (three such racks are provided in a linear array in the currently preferred embodiment of the invention). The motor does not move the camera during the period when the camera is viewing a specific rack. The camera sees a 2-dimensional picture of the rack and thus can see the entire aspect of each tube in a rack. After reading one rack, the camera is moved by the motor to view the next rack. Also, associated with the rack 1 is a rotary mounting fixture including a rotary platform or drum carrying supporting formations which enable the rack 1 to be safely retained on the mounting fixture as this is rotated about a horizontal axis XR under the action of motor means (not shown). Thus, the rack 1 and the tube or tubes T located therein are vertically rotated about an axis XR to achieve thorough mixing of the specimen immediately before initiating the optical reading. The rack 1 also allows the tube or tubes T to be optically observed from the side starting immediately above the blood/air meniscus and continuing downward over a distance defining a window W as explained in detail in the following.

Even though preferred at present, the rack arrangement described in the foregoing is not—per se—critical to the invention. Other arrangements, such as the one currently used in the SEDISCAN$^R$ system, can be used. This also applies to the nature of the imaging device embodied by the video camera 3. As an alternative to LCDs, linear CCD arrays and other devices (including non-optical devices) may be used.

Also, the arrangement for causing the camera 3 to move along the rack array, as well as the rotary mounting fixture for the racks 1, are conventional in the art and do not require to be described in further detail.

The foregoing also applies—in general terms—to the computer-controlled arrangement adopted for processing the output signal from the camera 3 and the possibility of using a manual scanner 10 for identifying each and every tube T as it is loaded into the respective rack 1. The manual scanner 10 enables each patient's identification data (usually in the form of a bar code) to be read from a label L applied around the lower portion of each tube T when collecting the blood samples. Both the output signal (which is usually converted to a digital format) as well the signal from the manual scanner 10 are fed to a data processing unit, such as a personal computer 11. As an alternative to a programmed general purpose computers, a dedicated computer or processor can be used. Suitable programming (according to well-known criteria which are not required to be described here) enables each tube T to be safely identified as such, prior to loading into the instrument, while the respective camera reading 3, converted to a standard Westergren value, can be outputted as a visual display on a screen and/or a hard copy printout or communicated electronically to the host computer managing patient data in the laboratory. For a general review of the general principles of operation of such a processing unit, reference may be made to the User's Guide to the SEDIS© software available with Becton Dickinson Vacutainer Systems and Cell Science Product Europe for use with the SEDISCAN$^R$ measuring system. Further details concerning the algorithm adopted for converting the camera reading 3 to standard of Westergren values are provided in the following.

When a plurality of tubes (such as fifteen tubes) T are tested simultaneously in a rack, these are preferably arranged in the rack in an array including two parallel rows, as shown in FIG. 2, with the tubes T in the adjacent rows suitably staggered or offset in order to make sure that all the tubes T in the two-row array can be inspected by the camera 3 moving along a line parallel to the two rows.

Preferably, the locations of the tubes in each rack 1 are such that all the tubes in the rack can be inspected simultaneously by the camera 3 positioned at a given point with respect of the rack 1. That point is preferably chosen to correspond to a central positioning of the camera 3 with respect to the length of the rack.

As the tubes in each rack 1 can be viewed simultaneously by the camera 3 from a single location, the camera 3 needs to be stopped only once for each rack, without any scanning movement being required. In the presently preferred embodiment of the invention, three racks are arranged to be tested simultaneously, and the movement of the camera 3 along the guide 3a is thus stopped three times. Suitable controls may however be provided in order to prevent the camera from stopping at any location where, for any reasons, no rack, a rack containing no tubes or a rack containing only empty tubes are arranged.

From FIG. 3 it will be appreciated that, in the preferred embodiment of the invention, the tubes T are held inclined at an angle a with respect to the vertical.

As the classic Westergren method specifies that the specimen be examined after remaining vertically upright for 60 or 120 minutes, the clinician or laboratorian must wait this long before providing a diagnostic result for the patient. This inevitably results in inefficiencies and high costs in the health care environment, where it is the primary goal of the health care to provide to deliver care as rapidly and cost effectively as possible.

It was found that the ESR is artificially accelerated if the tube T is inclined from the classical vertical position. This fact was already recognised in the past as witnessed e.g. from textbooks such as "Clinical Haematology, 5th edition" 1961 (Wintrobe) or "Todd-Stanford clinical diagnosis by lab methods" 14 edition, 1969 (Davidsohn & Henry).

While the underlying mechanism is not thoroughly clear, it is felt that, by keeping the tube T inclined with respect to the vertical position, the blood cells descend along the tube wall and accelerate more rapidly than the classic vertical position, while the plasma ascends.

In the arrangement shown in FIG. 3, this result can be easily achieved simply by stopping the rotary motion of the mounting fixture carrying the rack 1 at the end of the mixing stage at a position which leaves the tube(s) T oriented approximately 20° from the vertical position. For that purpose reference indicia (such as a notch or an optical mark 12) can be provided on the rotary fixture carrying the racks 1. Such indicia are detected by respective sensors 12a (of known type), acting as angular position sensing means, in order to stop the rotary motion of the fixture at the desired angular position.

An inclination angle of about 20° was experimentally found to represent an optimal choice. While in principle significantly different inclinations can be used, it was found that lower angles will not accelerate the sedimentation rate as much and have been seen to result in poorer reproducibility of the measurement. Higher angles offer slight improvements in the rate of sedimentation, but create distortion for the optical viewing device (e.g. the camera 3) in sensing the specimen, particularly in the area of the blood/air meniscus defining the top of the blood column which changes shape from a circle to an ellipse in a cylindrical tube the more inclined the tube becomes. This may result in a poor establishment of the zero or base line from which the ESR measurement is based.

In the classic Westergren method, a 200 mm long tube is scanned after 60 or 120 minutes. Depending upon such variables as patients' health, sex, age and haematocrit, it may be necessary to scan the tube for the cell/plasma interface as far down as 150 mm below the meniscus. Because the rate at which the cells fall is very slow, particularly in the vertical position, the operator must wait at least 60 minutes before he or she can be certain that the rate of a cell falling has effectively reached zero. The size, cost and complexity of an instrument to accurately search for and locate the cell/plasma interface is increased by having to examine such a long distance as 150 mm.

As opposed thereto, in the arrangement of the invention a much smaller length or "window" W of the tube T containing the specimen is scanned.

In the solution of the invention a short blood collection tube (about 80 mm to about 110 mm, about 80 mm being the presently preferred value) is used whereby a blood column may be formed therein having a height of not less than about 75 mm and not more than about 105 mm. The tube is preferably inclined at approximately 20° to accelerate the rate at which the cells fall, making it possible to read significant displacements in the cell/plasma interface sooner than 60 minutes (preferably about 20 minutes or less). In addition, the optical viewing device is sized or adjusted only to read a short length (30–40 mm or less contrary to 70–80 mm of the SEDISCAN$^R$ system) of the tube T located at the top thereof, "at the top" meaning a length or window W which encompasses the blood/air meniscus in the tube T upon starting the test or has its upper margin lower than the blood air/meniscus and located in proximity thereto.

It will be appreciated that, in the exemplary embodiment of the invention shown, displacements in the cell/plasma interface are simply read or viewed by the camera 3 without any vertical scanning movement along the test tubes being required.

In a thoroughly unexpected manner, it was found that by restricting the distance the cells have fallen to said reduced length W and at said periods, the observed values are representative—with a high degree of reliability and repeatability—of the desired ESR values. Consequently, by transforming the observed values, final values can be found which closely match the classic Westergren values.

Preferably, if the cell/plasma interface remains in the viewed length W for the entire test period (20 minutes or less), the final observed value are used for conversion to the classic Westergren value. Also preferably, if the cells have fallen at such a rapid rate, that the interface is outside of the length W before the end of the total test period the previous observed reading which fell within the viewed length W is used for conversion to the classic Westergren value. Thus, by observing only a small portion of the tube below the blood/air meniscus and converting the observed value to a classic Westergren value in far less than 60–120 minutes, the invention provides a solution for giving thoroughly reliable results to the patient in a much faster period than in the past.

As indicated in the foregoing, attempts were already made in the past of using shorter test tubes (i.e. shorter blood columns) and/or providing results in a shorter time than the standard 60–120 minutes of the Westergren method. None the less, these past methods require the whole blood column, or a substantial portion thereof (about 70–80%), to be scanned in order to obtain reliable results.

Contrary to any expectation, the solution of the invention provides for cell falling being monitored only over a reduced length or window of the blood column in the tube while providing thoroughly reliable results even if the overall period the cell falling phenomenon is observed is reduced to 20 minutes or less.

Another less apparent, but extremely important advantage of the solution of the invention, is that because the window W is only a portion of the entire tube length (see especially FIG. 1) the remaining tube length can be used to apply patient identification labels L to ensure the diagnostic result is properly matched by the laboratorian to the correct patient. This is particularly important as the use of bar code style positive patient identification labels L adapted for reading by manual scanners, such as scanner 10, has increased rapidly in an effort by hospitals to improve quality of care while increasing laboratory efficiency and throughput. These labels L are typically a 30–50 mm long (in the axial direction of the tube T). When these labels L are applied to "short" blood collection tubes T intended for ESR determination, they would cover such a large area of the tube T that is not possible to observe the meniscus or the interface in order to make the ESR measurement. As a result, these labels cannot be used or must be removed or the specimen must be transferred over to another tube T or pipette in order to make the ESR determination, or require (as is the case of the Diesse VESMATIC system referred to in the introductory portion of the description) to provide for an additional plastic outer sleeve to apply patient bar code or identification labels. This increases the opportunity for error, takes time, costs more money and/or exposes the laboratorian to a blood specimen unnecessarily.

Consequently, the present invention provides the significant advantage of being able to apply typical labels L onto the exterior of a primary tube for an ESR determination in an area (the lower portion of the tube T shown in FIG. 1) which does not obstruct the measurement. This is essentially due to the fact that—according to the invention—only a minor portion ("minor" meaning about 50% or less, typically about 30% or less) of the blood column within the tube T is actually used for determination. The remaining lower portion of the blood column, while playing a role in the overall cell falling phenomena, can be covered by the label L as it will not be used for determination purposes.

In order to provide the clinician with an estimate of the classic Westergren value when using a short tube length and observing only a small portion of the tube and when providing a reading in 20 minutes or less, it is necessary to utilise a mathematical algorithm to establish the relation of the observed reading to the Westergren value. Such an algorithm was constructed using extensive experimental data. The resulting system was then examined by comparing actual 60 and 120 minutes Westergren values versus extrapolated Westergren values as predicted by the mathematical algorithm.

Specifically, to establish the relationship, specimens from a large population of patients (n=101) admitted for hospitalization or seeking medical care were analysed by both the Westergren reference method and by the system. The sedimentation rate expressed in mm/hr for the Westergren reference method was collected using the standard glass pipette at the specified time intervals of 60 and 120 minutes after initiation of the test. Meanwhile, in parallel, using the instrument and tube previously described, the initial blood meniscus height in the tube at time 0 was determined. Subsequently, the location of the cell/plasma interface was observed via the camera system and measured by the instrument. This data was collected at intervals of about 10, 15 and 20 minutes after the initial time.

Figure 4:
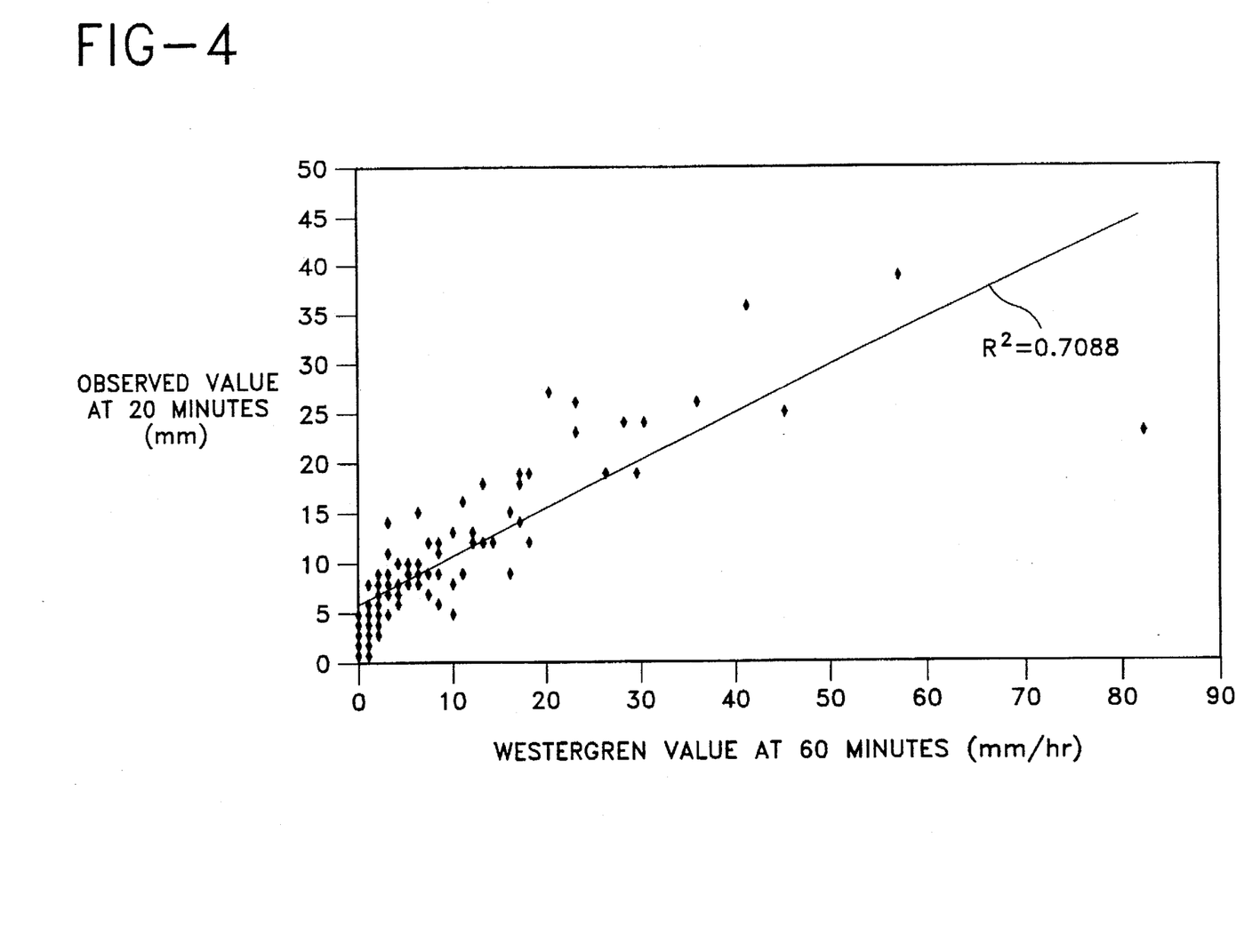
FIGS. 4 to 7 show the correlation between the results of the method of the invention and the results which would be obtained using the classical Westergren method.

Using a linear regression analysis, this data was first analyzed graphically by plotting the observed value at each time interval versus the reference method value and determining the correlation. An example of this data may be seen in FIG. 4. This shows that the correlation is reasonable ($R^2$=0.7088) as the flow data is actually non-linear. It was also confirmed that all of the observed cell/plasma meniscus had fallen less than about 38 mm from the initial starting blood column height of approximately 82 mm (46%). From this it was confirmed that in the system of the invention the sedimentation rate of the cells is such that it is possible to predict the Westergren value in 20 minutes or less. From this it was also confirmed that rather than observing a substantial length of the tube (i.e. 75% of the blood column height), that the blood/cell meniscus need only be observed at the 10, 15 and 20 minute time intervals within only approximately the upper 50% of the blood column height for nearly all the blood specimens. Therefore, it was not necessary to use the lower portion of the tube for observation.

Figure 5:
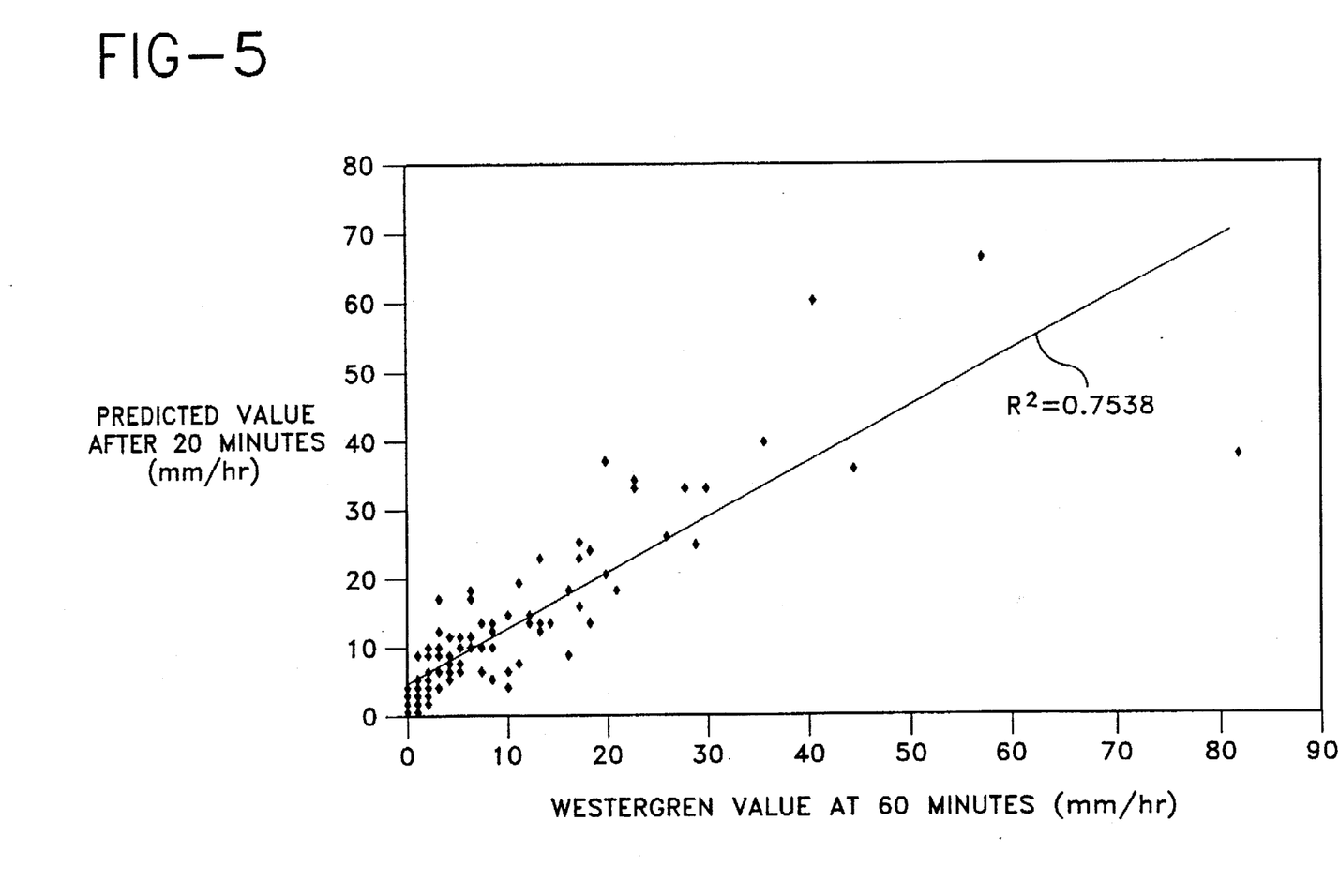

To further enhance the quality of the correlation achieved by observing only a limited portion of the blood column height at time intervals no later than 20 minutes after start of the test, non-linear polynomial algorithms were then chosen. In addition, it was learned that the correlation can be further enhanced by using two sets of such algorithms depending upon the initial column height of the tube. Tubes which were properly filled, in our case at greater than about 80 mm are analyzed using one algorithm to predict the Westergren value while tubes filled less than about 80 mm are analyzed using a second algorithm to predict the Westergren value. An example of this data may be seen in FIG. 5. Using a multiple part non-linear algorithm described in Tables 1 and 2, the observed data was converted and it was demonstrated that the correlation was improved ($R^2$=0.7536) and that the flow of data now follows the regression more closely.

To further enhance the quality of the correlation, clinical investigations were expanded to cover a population of 339 patients at multiple sites. The resulting algorithm is defined in Tables 1 and 2.

Table 1
Algorithm for Predicting the 60 minute Westergren value when blood column height is greater than 80 mm.

If cell/plasma meniscus (i.e. interface) has fallen <35 mm at 20 minute reading interval:
Predicted value (mm/hr)=$(0.652194*A)+(0.045525*A^2)-(0.06051*C^2)$ If cell/plasma meniscus has fallen >35 mm at 20 minute reading interval but <35 mm at 15 minute reading interval
Predicted value (mm/hr)=$(3.229994*B)-(0.0758*C^2)$ If cell/plasma meniscus has fallen >35 mm at 15 minute reading interval but <35 mm at 10 minute reading interval
Predicted value (mm/hr)=$(5.634304*A)-(0.07907*C^2)$ Algorithm for predicting the 60 minute Westergren value when blood column height is less than 80 mm.

If cell/plasma meniscus has fallen <30 mm at 20 minute reading interval:
Predicted value (mm/hr)=$(0.652194*A)+(0.045525*A^2)-(0.06051*C^2)$ If cell/plasma meniscus has fallen >30 mm at 20 minute reading interval but <30 mm at 15 minute reading interval:
Predicted value (mm/hr)=$(3.578074*B)-(2.1702*C^2)$ If cell/plasma meniscus has fallen >30 mm at 15 minute reading interval but <30 mm at 10 minute reading interval
Predicted value (mm/hr)=$(5.509347*C)-(0.08674*C^2)$ Where:
A=observed reading at 20 minute interval
B=observed reading at 15 minute interval
C=observed reading at 10 minute interval Table 2
Algorithm for predicting the 120 minute Westergren value when blood column height is greater than 80 mm.

If cell/plasma meniscus has fallen <35 mm at 20 minute reading interval:
Predicted value (mm/hr)=$(5.53835364*A)+(0.021903042*A^2)-(4.105250868*B^2)$ If cell/plasma meniscus has fallen >35 mm at 20 minute reading interval but <35 mm at 15 minute reading interval
Predicted value (mm/hr)=$(4.625610738*B)-(0.072863681*C^2)$ If cell/plasma meniscus has fallen >35 mm at 15 minute reading interval but <35 mm at 10 minute reading interval
Predicted value (mm/hr)=$(9.295466293*C)-(0.162433073*C^2)$ Algorithm for predicting the 60 minute Westergren value when blood column height is less than 80 mm.

Figure 6:
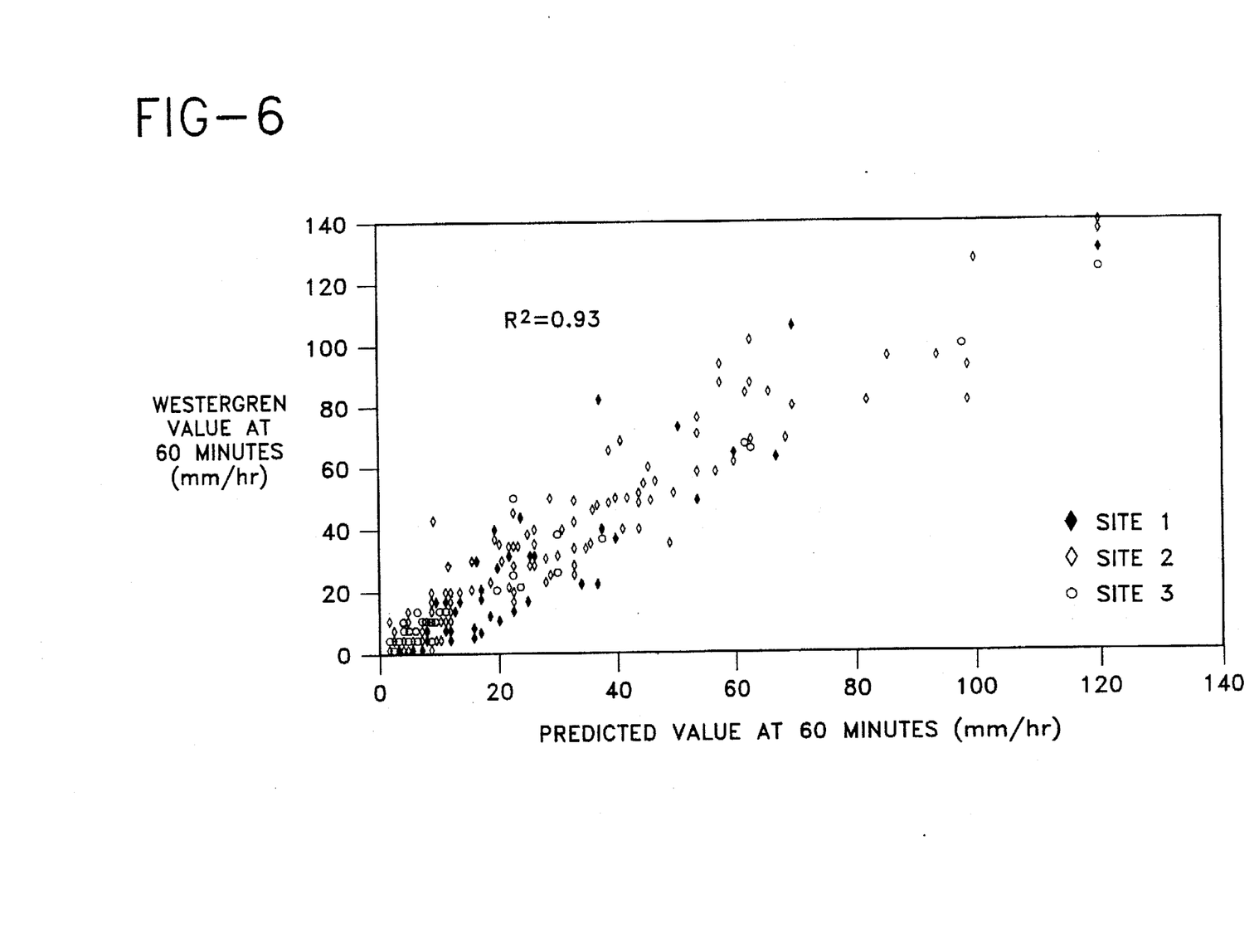
Figure 7:
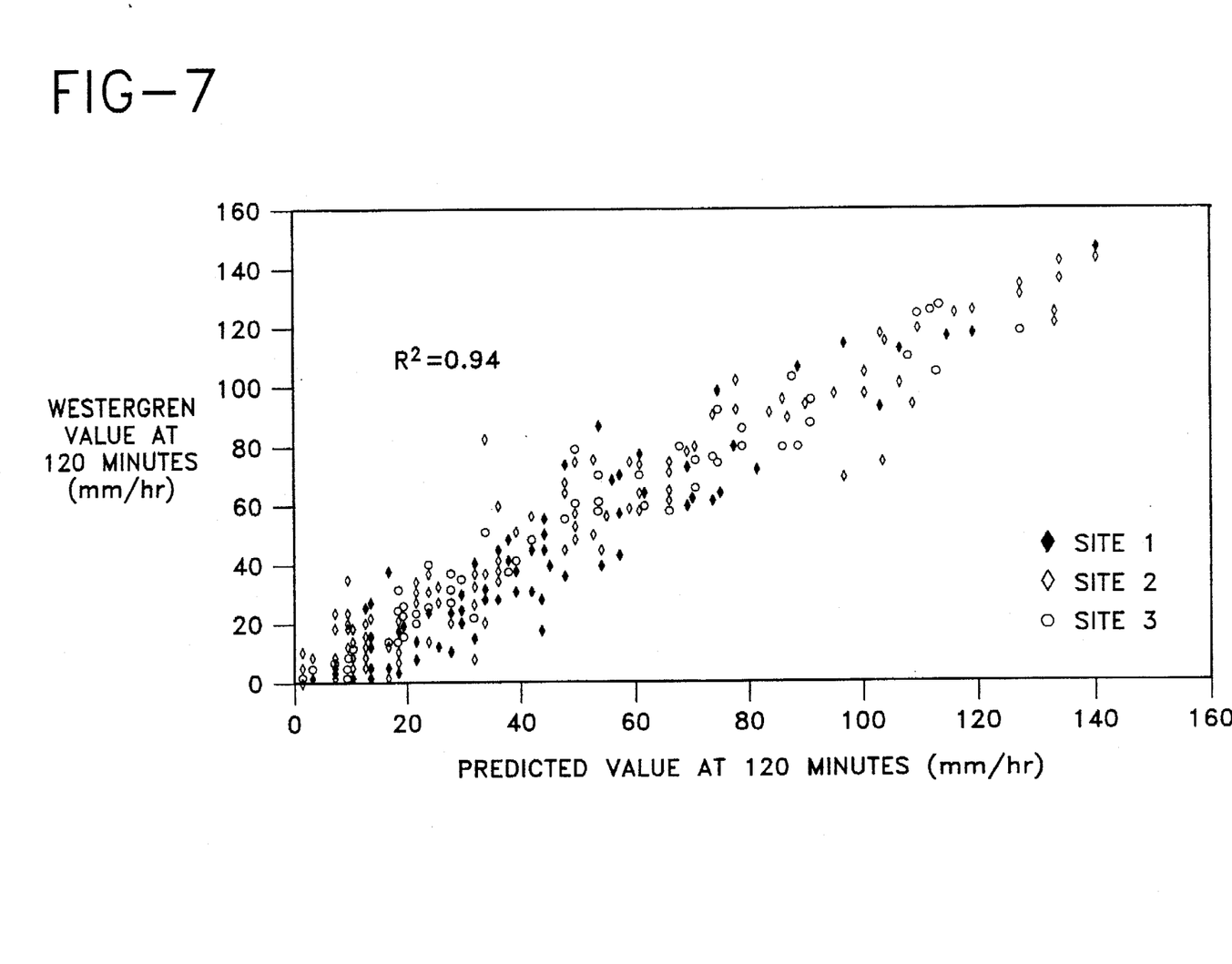

If cell/plasma meniscus has fallen <30 mm at 20 minute reading interval:
Predicted value (mm/hr)=$(5.53835364*A)+(0.021903042*A^2)-(4.105250868*B^2)$ If cell/plasma meniscus has fallen >30 mm at 20 minute reading interval but <30 mm at 15 minute reading interval:
Predicted value (mm/hr)=$(5.527322594*B)-(2.740388301*C^2)$ If cell/plasma meniscus has fallen >30 mm at 15 minute reading interval but <30 mm at 10 minute reading interval
Predicted value (mm/hr)=$(9.660137741*C)-(0.183986082*C^2)$ Where:
A=observed reading at 20 minute interval
B=observed reading at 15 minute interval
C=observed reading at 10 minute interval The correlation results achieved between the predicted value and the Westergren reference method may be seen in FIGS. 6 and 7 ($R^2$=0.93 for 60 minute Westergren value and $R^2$=0.94 for 120 minute Westergren value).

It will be easily appreciated that the various parameters considered in the foregoing (i.e. the 80 mm blood column height, the 35 mm distance fallen, the 10, 15, and 20 minute reading intervals), while constituting preferred choices at present, do not represent absolute imperative values. For that reason the wording "about" was resorted to in the annexed claims in respect of those parameters in order to make it clear that any possible minor changes, with respect to any of those parameters will not invalidate the expected results.

Also, it is entirely possible to develop alternatives to the algorithm presented herein that may be equally as effective. For example, the reading intervals can be chosen to be more frequent or less frequent than the 10,15 and 20 minute intervals described here. Consequently, the preferred coefficients disclosed in Tables 1 and 2 may vary accordingly. The system described here provides predictions after 20 minutes for the Westergren value classically obtained using the reference method after 60 and 120 minutes. The new system clearly offers significant advantage to the user by providing diagnostic values faster to the clinicians. By shortening the reading cycle further through the development of alternative algorithms in the manner described herein or in similar manners, it would further add advantage for the clinician.

It is also entirely possible to develop algorithms with mathematical corrections for environmental factors encountered during the test. Such factors may include the laboratory temperature as it is well established that increasing temperatures can accelerate the sedimentation rate.

It also possible to develop algorithms with mathematical correction for patient factors affecting the blood specimen. Such factors may include the patient haematocrit as it is well established that decreasing haematocrit can accelerate the sedimentation rate.

It is also possible to develop algorithms to achieve the desired correlation if one were to use specimen collection tubes of geometries and volumes or with additives other than described herein. For example: alternative surfactant; alternative citrate anticoagulant to blood ratios; alternative anticoagulants such as EDTA, heparin or hirudin; alternative tube diameters, shapes or lengths. Changes to any of these factors is likely to make the algorithms described herein less optimal. However, using the method described herein or similar methods, new algorithms can easily be developed, without undue experimentation being required, the key point being the recognition that the values obtained according to the invention are representative— with a high degree of reliability and repeatability—of the desired ESR values. Consequently, the values obtained can be converted, through a given relationship (as the algorithms disclosed in the foregoing) to the classic Westergren values.

Also, it will be easily appreciated that any conversion algorithm as those disclosed and/or referred to in the foregoing may be easily stored and implemented (in a thoroughly known manner) in a computer such as the computer designated 11 in FIG. 3.

We claim:

1. An apparatus for determining the erythrocyte sedimentation rate in a blood sample comprising:

at least one test tube comprising a blood sample comprising an open top end, a closed bottom end, a cylindrical sidewall having an inner surface and an outer surface extending between said open top end and said closed bottom end having a length of about 80 mm to about 110 mm, an outside diameter of about 7 mm to about 9 mm and an inside diameter of about 5 mm to about 7 mm, a stopper in said open top end, a label located near said closed bottom end on said outer surface of said sidewall comprising an upper portion and a lower portion and a window from about 30 mm to about 40 mm located between said open top end and said upper portion of said label;

at least one rack for receiving at least one of said test tube comprising a C-shaped frame comprising opposite lower and upper horizontal arms for receiving said tube, an upright arm extending between said lower and upper horizontal arms, a hinge connecting said upright arm and said lower horizontal arm, a fixed point connecting said upper horizontal arm and said upright arm, and a thumb-actuated slider lock mechanism on said upright arm, whereby when said tube is loaded into said rack, said rack is then locked in a closed position by said thumb-actuated slider lock mechanism;

a rotary mounting fixture comprising a rotary platform and a drive means connected to said rack whereby said rack is vertically rotated and then inclined at approximately 20° from the vertical position;

a background illumination source;

a detector means for viewing said blood sample in said tube in said rack in said window as a contrasted image against said background illumination source and supplying a first output signal;

a drive means for carrying said detector means in a traverse movement along said tube;

a manual scanner for reading said label on said tube and supplying a second output signal; and a data processing unit for receiving said first output signal from said detector means and said second output signal from said manual scanner and converting said first output signal to a digital format to calculate the erythrocyte sedimentation rate of said blood sample of said test tube.

2. A method for determining the erythrocyte sedimentation rate in a blood sample, comprising the steps of:

(a) providing a blood sample having a blood column height of about 75 mm to about 105 mm and a diameter of about 5 mm to about 7 mm in a tube comprising an open top end, a closed bottom end, a cylindrical sidewall having an inner surface and an outer surface extending between said open top end and said closed bottom end having a length of about 80 mm to about 110 mm, an outside diameter of about 7 mm to about 9 mm and an inside diameter of about 5 mm to about 7 mm, a stopper in said open top end, a label located near said closed bottom end on said outer surface of said sidewall comprising an upper portion and a lower portion and a window from about 30 mm to about 40 mm located between said open top end and said upper portion of said label.

(b) mixing said blood sample in said tube by vertically rotating said tube;

(c) inclining said rube at approximately 20° to the vertical whereby said blood column is also inclined at about 20° with respect to the vertical;

(d) viewing said blood sample in said tube at said window to detect the blood/air meniscus interface of said blood sample at an initial time and to detect said height of said blood column;

(e) detecting the location of the cell/plasma interface of said blood sample at said window at least about 20 minutes after step (d); and (f) converting the location of the cell/plasma interface of step (e) and said height of said blood column of step (d) into a standard Westergren value for erythrocyte sedimentation rate by polynomial interpolation.

3. A method for determining the erythrocyte sedimentation rate in a blood sample, comprising the steps of:

(a) providing a blood sample having a blood column height of about 75 mm to about 105 mm and a diameter of about 5 mm to about 7 mm in a tube comprising an open top end, a closed bottom end, a cylindrical sidewall having an inner surface and an outer surface extending between said open top end and said closed bottom end having a length of about 80 mm to about 110 mm, an outside diameter of about 7 mm to about 9 mm and an inside diameter of about 5 mm to about 7 mm, a stopper in said open top end, a label located near said closed bottom end on said outer surface of said sidewall comprising an upper portion and a lower portion and a window from about 30 mm to about 40 mm located between said open top end and said upper portion of said label;

(b) mixing said blood sample in said tube by vertically rotating said tube;

(c) inclining said tube at approximately 20° to the vertical whereby said blood column is also inclined at about 20° with respect to the vertical;

(d) viewing said blood sample in said tube at said window to detect the blood/air meniscus interface of said blood sample at an initial time and to detect said height of said blood column;

(e) detecting the first interval location of the cell/plasma interface of said blood sample at said window at least about 5 minutes after step (d);

(f) detecting the second interval location of the cell/plasma interface of said blood sample at said window at least about 5 minutes after step (e);

(g) detecting the third interval location of the cell/plasma interface of said blood sample at said window at least about 5 minutes after step (f);

(h) converting said locations of the cell/plasma interfaces of steps (e), (f) and (g) and said height of said blood column of step (d) into a standard Westergren value for erythrocyte sedimentation rate by polynomial interpolation.

4. The method of claim 3, wherein said standard Westergren value is computed as a predicted 60 minute Westergren value as follows:

a) if said height of said blood column is greater than about 80 mm then:

(i) If said cell/plasma interface has fallen about <35 mm at said first interval location then:

Predicted value (mm/hr)=$(a1 \times A)+(a2 \times A^2)-(a3 \times C^2)$; or (ii) If said cell/plasma interface has fallen>about 35 mm at said first location interval but<about 35 mm at said second interval location then:

Predicted value (mm/hr)=$(a4 \times B)-(a5 \times C^2)$; or (iii) If said cell/plasma interface has fallen>about 35 mm at said second interval location but<about 35 mm at said third interval location then:

Predicted value (mm/hr)=$(a6 \times A)-(a7 \times C^2)$;

b) if said height of said blood column height is less than about 80 mm then:

(i) If said cell/plasma interface has fallen>about 30 mm at said first interval location then:

Predicted value (mm/hr)=$(a1 \times A)+(a2 \times A^2)-(a3 \times C^2)$; or

If said cell/plasma interface has fallen>about 30 mm at said first interval location but<about 30 mm at said second interval location then:

Predicted value (mm/hr)=$(a8 \times B)-(a9 \times C)$; or

If said cell/plasma interface has fallen>about 30 mm at said second interval location but<about 30 mm at said third interval location then:

Predicted value (mm/hr)=$(a10 \times C)-(a11 \times C^2)$;

where:
A=observed reading at said first interval location;
B=observed reading at said second interval location;
C=observed reading at said third interval location; and a1-a11 are constant values.

5. The method of claim 4, characterized in that said constant values (a1-a11) are as follows:

a1=0.652194
a2=0.045525
a3=0.06051
a4=3.229994
a5=0.0758
a6=5.634304
a7=0.07907
a8=3.578074
a9=2.1702
a10=5.509347
a11=0.08674

6. The method of claim 3, wherein said standard Westergren value is computed as a predicted 120 minute Westergren value as follows:

a) if said height of said blood column height is greater than about 80 mm then:

(i) If said cell/plasma interface has fallen<about 35 mm at said first interval location then:

Predicted value (mm/hr)=$(b1 \times A)+(b2 \times A2)-(b3 \times B2)$; or (ii) If said cell/plasma interface has fallen>about 35 mm at said first interval location but<about 35 mm at said second interval location then:

Predicted value (mm/hr)=$(b4 \times B)-(b5 \times C^2)$; or (iii) If said cell/plasma interface has fallen>about 35 mm at said second interval location but<about 35 mm at said third interval location then:

Predicted value (mm/hr)=$(b6 \times C)-(b7 \times C^2)$;

b) if said height of said blood column is less than about 80 mm then:

(i) If said cell/plasma interface has fallen<about 30 mm at said first interval location then:

Predicted value (mm/hr)=$(bi \times A)+(b2 \times A2)-(b3 \times B^2)$; or (ii) If said cell/plasma interface has fallen>about 30 mm at said first interval location but<about 30 mm at said second interval location then:

Predicted value (mm/hr)=$(b8 \times B)-(b9 \times C)$; or (iii) If said cell/plasma interface has fallen>about 30 mm at said second interval location but<about 30 mm at said third interval location then:

Predicted value (mm/hr)=(b10×C)−(b11×C²);

where:
A=observed reading at said first interval location;
B=observed reading at said second interval location;
C=observed reading at said third interval location; and b1-b11 are constant values.

7. The method of claim 6, characterized in that said constant values (b1-b11) are as follows:

b1=5.53835364
b2=0.021903042
b3=4.105250868
b4=4.625610738
b5=0.072863681
b6=9.295466293
b7=0.162433073
b8=5.527322594
b9=2.740388301
b10=9.660137741
b11=0.183986082

* * * * *